: US006458110B1

(12) United States Patent
Lavon et al.

(10) Patent No.: US 6,458,110 B1
(45) Date of Patent: Oct. 1, 2002

(54) DISPOSABLE ARTICLE HAVING AN EXPANDABLE COMPONENT

(75) Inventors: Gary D. Lavon, Cincinnati, OH (US); William R. Vinnage, Jr., Cincinnati, OH (US); Letha M. Hines, Cincinnati, OH (US); Donald C. Roe, West Chester, OH (US); Brandon E. Wise, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/481,457

(22) Filed: Jan. 11, 2000

(51) Int. Cl.[7] ............................................... A61F 13/15
(52) U.S. Cl. .............................. 604/385.01; 604/385.12
(58) Field of Search ...................... 604/385.01, 385.08, 604/369, 358, 373, 327, 385.101, 385.12, 379

(56) References Cited

U.S. PATENT DOCUMENTS

| 3,512,528 A | 5/1970 | Whitehead et al. ......... 128/285 |
| 3,921,232 A | 11/1975 | Whyte ............................. 5/91 |
| 4,781,645 A | 11/1988 | Kato .......................... 446/188 |
| 4,929,214 A | 5/1990 | Liebermann ................. 446/221 |
| 5,306,266 A | 4/1994 | Freeland ................... 604/385.1 |
| 5,330,459 A | 7/1994 | Lavon et al. ............ 604/385.1 |
| 5,520,674 A | 5/1996 | Lavon et al. |
| 5,876,393 A | 3/1999 | Ahr et al. .................... 604/387 |
| 5,997,520 A | 12/1999 | Ahr et al. ................ 604/385.1 |

FOREIGN PATENT DOCUMENTS

| DE | 3517192 A1 | 11/1986 | .......... A61F/13/16 |
| WO | WO00/00125 A1 | 1/2000 | |

Primary Examiner—Danny Worrell
(74) Attorney, Agent, or Firm—Michael S. Kolodesh; David M. Weirich; Steven W. Miller

(57) ABSTRACT

An absorbent article having an expandable component. The expandable component comprises a compressed, resilient element disposed within an air impermeable envelope. The compressed element provides the absorbent article with a thin, low bulk profile prior to use of the disposable absorbent article, thereby reducing shipping and storage space. The user may open the impervious envelope, thereby permitting entry of air into the envelope and expansion of the compressed element. In one embodiment the expandable component is a spacer for maintaining fecal void space in a disposable diaper. Alternatively, the expandable component can provide displacement of the topsheet relative to the backsheet along the longitudinal centerline of a sanitary napkin.

25 Claims, 6 Drawing Sheets

DISPOSABLE ARTICLE HAVING AN EXPANDABLE COMPONENT

FIELD OF THE INVENTION

The present invention is related to disposable absorbent articles having a consumer activated component that is expandable.

BACKGROUND OF THE INVENTION

Disposable absorbent articles are used to absorb and retain body exudates, such as urine, fecal material, menses, and the like. A particular desired feature of disposable absorbent articles is the capability to acquire and hold body exudates to minimize leakage of body exudates from between the absorbent article and the wearer.

References in the art teach adding a spacer to the disposable absorbent article for aiding in the containment of fecal material. Such spacers suffer from the disadvantage that they increase the initial thickness of the disposable absorbent article, and thereby increase shipping and storage costs. Such spacers may also be perceived by consumers to be uncomfortable because of their thickness prior to application of the diaper to the wearer. Examples of spacers are shown in the following references: U.S. Pat. No. 5,176,672 issued Jan. 5, 1993 to Bruemmer et al., U.S. Pat. No. 5,171,236 issued Dec. 15, 1992 to Dreier et al., and U.S. patent application Ser. No. 08/698,471, Spacers for Use in Disposable Absorbent Articles and Disposable Absorbent Articles Having Such Spacers, filed Aug. 15, 1996 by Allen et al.

Still other references disclose absorbent articles having inflatable structures. French Patent Application 2,561,078 published Sep. 20, 1985 in the name of Lefebvre discloses a diaper having a structure which is inflatable by mouth. Such inflation can be awkward or inconvenient, especially in public areas or when the diaper is already fastened to the wearer. Such an arrangement is also disadvantageous because of sanitary considerations.

U.S. Pat. Nos. 3,881,491 and 3,921,232 issued to Whyte on May 6, 1975 and Nov. 25, 1975 respectively, disclose disposable absorbent articles having self is inflating structures. The self inflating structures include a wall of semi-permeable material through which body fluids can pass, and a gas evolving material which interacts with an activator material (e.g., urine) to inflate the structure. The structure taught by Whyte primarily prevents core densification and suffers from the disadvantage that it requires an activator material from an external source, such as urine. The wearer may not urinate at the desired time, in the desired location, or in the desired amount to properly inflate the structure. U.S. Pat. No. 5,876,393 issued Mar. 2, 1999 to Ahr et al. and U.S. Pat. No. 5,530,459 issued Jul. 19, 1994 to LaVon et al. disclose inflatable diaper components whose inflation requires wetting of the component or mixture of two different materials.

Accordingly, it would be desirable to provide a disposable absorbent article having a component that is expandable by a wearer, or by a person caring for the wearer, before or after the absorbent article is fastened to the wearer. It would also be desirable to provide a diaper having a spacer for maintaining a fecal void space, wherein the spacer thickness can be increased without the need for wetting of the spacer, and wherein the spacer thickness can be activated at a time selected by the consumer or wearer. Further, it would be advantageous to provide a sanitary napkin embodiment of the present invention having a component which is expandable to provide separation and lift of the topsheet and core relative to the backsheet of the sanitary napkin, and increase the caliper of the sanitary napkin along the longitudinal centerline of the sanitary napkin.

SUMMARY OF THE INVENTION

In order to solve the problems of the prior art, the present invention provides a disposable absorbent article having a topsheet, a backsheet, an absorbent core disposed intermediate the topsheet and backsheet, and an expandable component. In a preferred embodiment, the expandable component comprises a compressed resilient element disposed within an air impermeable envelope. The air impermeable envelope can be evacuated, such as by vacuum sealing, to have an internal pressure less than the outside atmospheric pressure. The expandable component expands from a first thickness to a second thickness greater than the first thickness upon opening of the air impermeable envelope.

The air impermeable envelope can comprise a port having a releasable closure. The releasable closure can be removed at the point of use of the disposable absorbent article to permit air to enter the envelope through the port, thereby providing expansion of the expandable component. In one embodiment, the releasable closure can be resealable, so that air drawn into the port does not escape when the expandable component is subjected to compressive loading.

In certain preferred embodiments of the present invention, the port may comprise a gas-permeable component such as a gas-permeable membrane or film. The rate of expansion of the expandable component may be controlled by varying the diffusion rate of the gas-permeable membrane and the port area.

The expandable component can be positioned on the body facing surface of the topsheet, on the garment facing surface of the backsheet, or between the topsheet and the backsheet. In one embodiment the expandable component is disposed intermediate the backsheet and the absorbent core. The expandable component can comprise a spacer for maintaining a fecal void space in a disposable diaper. Alternatively, the expandable component can provide a seal in the waist regions or the side margins of a disposable diaper. In another embodiment the expandable component is located along the longitudinal centerline of a sanitary napkin to provide lifting of the topsheet and core relative to the backsheet, and increased caliper of the sanitary napkin along the longitudinal centerline of the sanitary napkin.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates Ifs discharged from the body. Such absorbent articles include, but are not limited to, diapers, training pants, incontinence briefs, diaper holders, diaper liners, and feminine hygiene products such as sanitary napkins, pantiliners, and the like. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner).

Figure 1:
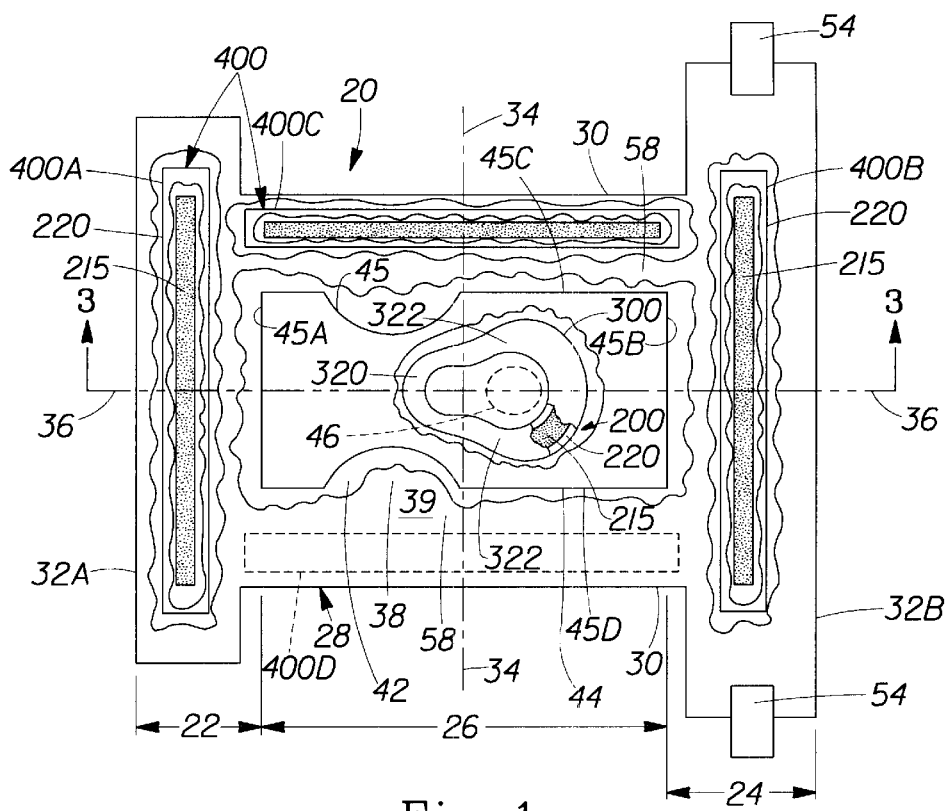
FIG. 1 is a top plan view of a disposable diaper with portions of the topsheet and absorbent core shown cutaway to illustrate expandable components, including a keyhole shaped spacer for maintaining a fecal void space, and seals positioned in the waist regions and side margins of the diaper.

One embodiment of an absorbent article of the present invention is the unitary disposable diaper 20, shown in FIG. 1. As used herein, the term "diaper" refers to an absorbent article generally worn by infants and incontinent persons that is worn about the lower torso of the wearer. FIG. 1 is a plan view of the diaper 20 of the present invention in its flat-out, uncontracted state (i.e., with elastic induced contraction pulled out) with portions of the structure being cutaway to more clearly show the construction of the diaper 20 and with the portion of the diaper 20 which faces or contacts the wearer, the inner surface, oriented towards the viewer. The diaper 20 is shown in FIG. 1 to have a front waist region 22, a rear waist region 24, a crotch region 26, and a periphery 28 comprising longitudinal edges 30 and front and rear lateral end edges 32A and 32B. The diaper 20 also has a lateral centerline 34 and a longitudinal centerline 36.

As used herein, the "longitudinal" dimension, direction, or axis of the diaper 20 is aligned front to back with respect to the wearer as the disposable absorbent article is worn. The "lateral" or "transverse" dimension, direction, or axis of the diaper 20 is orthogonal the longitudinal direction and is sideways aligned as the diaper 20 is worn. The "Z-direction" is orthogonal to both the longitudinal and transverse directions, and is illustrated in FIG. 3.

The front waist region 22 and the rear waist region 24 are those portions of the diaper 20 which, when worn, encircle the waist of the wearer and are generally the highest elevation of the diaper 20 when the wearer is in the standing position. The crotch region 26 is disposed between the front and rear waist regions 22, 24 and is that part of the diaper 20 which, when worn, is between the wearer's legs.

Figure 2:
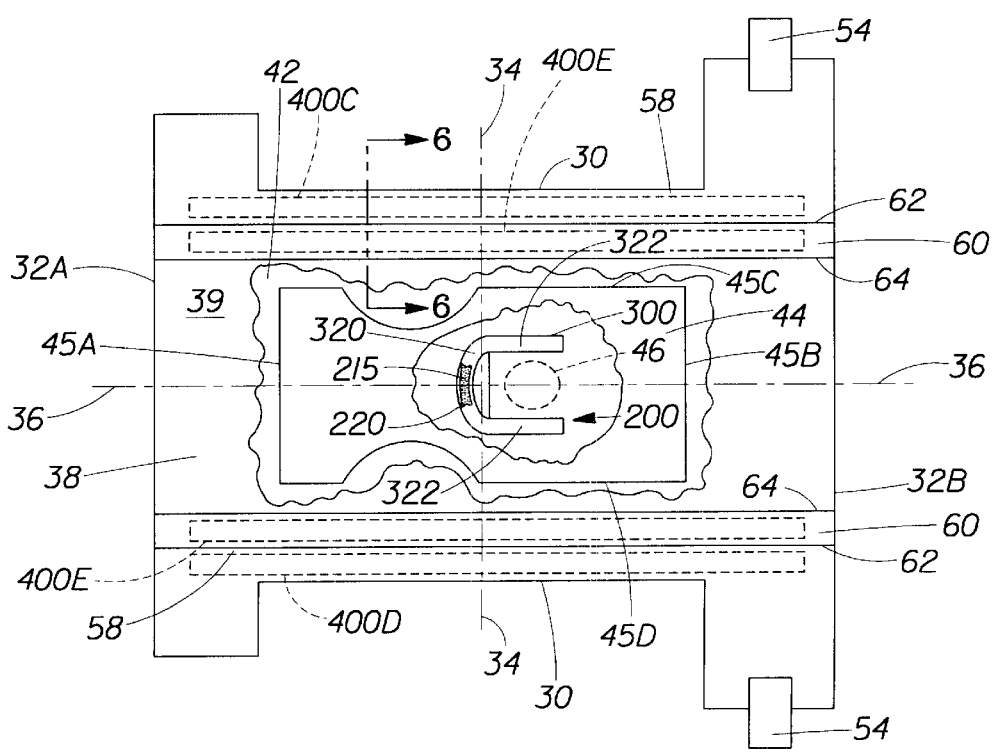
FIG. 2 is a top plan view of a disposable diaper similar to that of FIG. 1, with portions of the topsheet and absorbent core shown cutaway to illustrate an expandable component comprising a U-shaped spacer opening rearward, and with expandable components shown (in phantom) positioned to provide seals in the side margins, including seals on leg cuffs.
Figure 3:
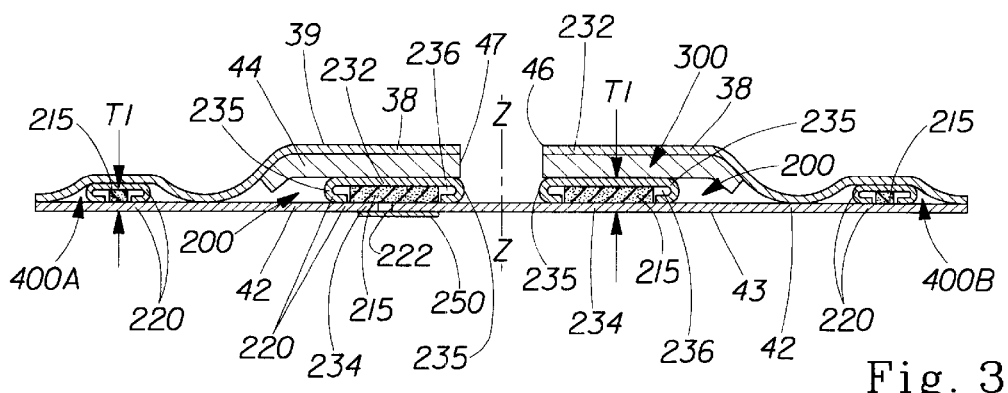
FIG. 3 is an sectional view taken along line 3—3 in FIG. 1 showing the expandable components in a compressed configuration.

As shown in FIGS. 1–3, the diaper 20 preferably comprises a liquid pervious topsheet 38, a liquid impervious backsheet 42, the backsheet 42 joined at least peripherally with the topsheet 38, and an absorbent core 44 disposed intermediate the topsheet 38 and the backsheet 42. The absorbent core 44 can comprise one or more layers, with one layer shown in the Figures. The absorbent core 44 has a perimeter 45 which includes front and rear laterally extending ends 45A and 45B, as well as side edges 45C and 45D. The diaper 20 has side margins 58 extending laterally from the absorbent core side edges 45C and 45D to the longitudinal edges 30 of the diaper 20. The side margins 58 include those portions of the topsheet 38 and/or backsheet 42 which extend laterally outward from the absorbent core side edges 45C and 45D.

The diaper 20 has a body facing surface 39 comprising that portion of the diaper 20 which is positioned adjacent to the wearer's body during use (i.e., the surface 39 generally is formed by at least a portion of the topsheet 38.) The diaper also has a garment facing surface 43 (FIG. 3) comprising that portion of the diaper 20 which is positioned away from the wearer's body (i.e., the garment facing 43 generally is formed by at least a portion of the backsheet 42, and can comprise other components joined to the backsheet 42.)

Figure 4:
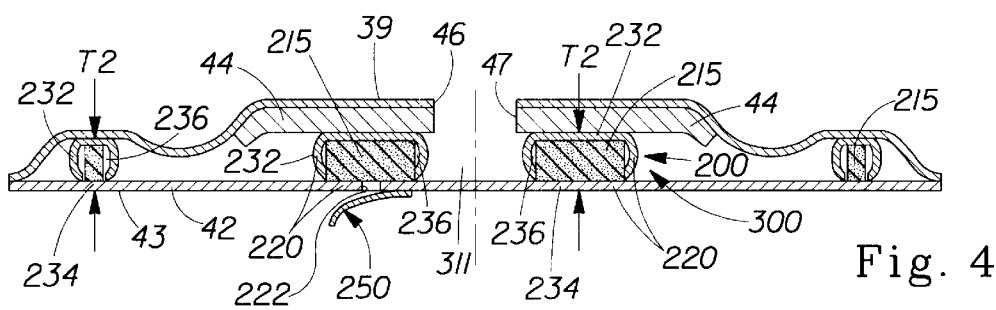
FIG. 4 is an sectional view similar to that of FIG. 3 showing the expandable components in an expanded configuration.

The diaper 20 according to the present invention also comprises at least one component 200 expandable from a compressed configuration having a first thickness T1 shown in FIG. 3, to an expanded configuration having a second thickness T2 greater than T1, as shown in FIG. 4. In the compressed configuration, the expandable component 200 comprises a compressed resilient element 215 disposed within an air impermeable envelope 220. The air impermeable envelope 220 can also comprise a port 222 having a releasable closure 250.

Without being limited by theory, it is believed that the compressed resilient element 215 does not expand within the sealed air impermeable envelope 220 because such expansion would increase the volume within the sealed air impermeable envelope 220; and thereby lower the air pressure within the sealed envelope 220. Accordingly, the relatively constant atmospheric pressure outside the sealed envelope 220 prevents expansion of the resilient element 215 within the sealed air impermeable envelope 220. Upon opening the air impermeable envelope 220, such as by releasing the closure 250 to permit air to enter the envelope 220 through the port 222, the expandable component 200 is expandable from the first thickness T1 in the compressed configuration shown in FIG. 3 to have a predetermined shape and a second thickness T2 (FIG. 4) greater than T1. The second thickness T2 is preferably at least about twice the thickness T1, and more preferably at least about five times the thickness T1.

By the term "compressed" it is meant that the element 215 has a reduced thickness within the sealed air impermeable envelope 220 which is less than the free, unrestrained thickness of the element 215. The reduced thickness of the resilient element 215 within the sealed envelope 220 is preferably no more than about one half the free, unrestrained thickness of the element 215. By "resilient" it is meant that the element 215 can be compressed (such as by a Z-direction compressive loading) from its free, unrestrained thickness to its reduced thickness, and that upon release of force maintaining the element 215 in a compressed configuration, the element 215 expands to have a thickness which is at least 70 percent, and preferably at least 85 percent of its free, unrestrained thickness within about 10 minutes.

The diaper 20 can also include a pair of fasteners 54, such as tape tabs or mechanical fasteners, positioned in the rear waist region 24 for fastening the diaper 20 to the wearer. The diaper can also have a waist elastic feature, gasket cuffs, and barrier leg cuffs 60 having a proximal edge 62 joined to a side margin 58 of the diaper 20, and distal edge 64 spaced from the topsheet 38. U.S. Pat. No. 3,848,594 issued Nov. 19, 1974 to Buell and U.S. Reissue Patent B14,662,875 reissued May 5, 1987 to Hirotsu et al. are incorporate herein by reference to illustrate suitable tape tab fasteners 54. U.S. Pat. No. 3,860,003 issued Jan. 14, 1975 to Buell; U.S. Pat. No. 4,081,301 issued Mar. 28, 1978 to Buell; U.S. Pat. No. 4,695,278 issued Sep. 22, 1987 to Lawson; and U.S. Pat. No. 4,938,755 issued Jul. 3, 1990 to Foreman are incorporated herein by reference to illustrate gasket cuffs and barrier leg cuffs 60. U.S. Pat. No. 4,515,595 issued May 17, 1985 to Kievit; and U.S. Pat. No. 4,816,025 issued Mar. 28, 1989 to Foreman are incorporated herein by reference to illustrate an elasticized waistband for a diaper 20.

In one embodiment, the expandable component 200 can comprise a spacer 300 disposed intermediate the topsheet 38 and the backsheet 42, as shown in FIGS. 1–4, for maintaining a Z-direction fecal void space 311. In the embodiment shown, the spacer 300 is disposed intermediate the absorbent core 44 and the backsheet 42. In another embodiment, the expandable component 200 can comprise seals, such as seals 400A and 400B for preventing leakage of body exudates from the front and rear waist regions 22 and 24, respectively, and seals 400C and 400D for preventing leakage of body exudates from the side margins 58. In yet another embodiment, the expandable component 200 can comprise seals 400E disposed on barrier leg cuffs 60, as shown in phantom in FIG. 2, and as shown in cross-section in FIG. 6.

Referring to the components of the diaper 20 in more detail, FIG. 1 shows an embodiment of the diaper 20 in which the topsheet 38 and the backsheet 42 have length and width dimensions generally larger than those of the absorbent core 44. The topsheet 38 and the backsheet 42 extend longitudinally beyond the laterally extending core ends 45A and 45B to form the front and rear waist regions 22 and 24. The topsheet 38 and backsheet 42 extend laterally beyond core side edges 45C and 45D to form side margins 58. While the topsheet 38, the backsheet 42 and the absorbent core 44 may be assembled in a variety of well known configurations, preferred diaper configurations are described generally in U.S. Pat. No. 3,860,003 issued to Buell on Jan. 14, 1975 and U.S. Pat. No. 5,151,092 issued to Buell on Sep. 29, 1992, each of which is incorporated herein by reference.

The spacer 300 illustrated in FIG. 1 has a generally "keyhole" shape comprising a closed figure. Other suitable closed shapes for the spacer 300 include, but are not limited to, circles, squares, and elongated shapes, such as ovals and rectangles. Alternatively, the spacer 300 can comprise an open figure, such as the generally U-shaped figure opening rearward shown in FIG. 2. The spacer 300 preferably includes a laterally extending portion 320 joining two longitudinally extending portions 322. Suitable shapes and dimensions for a spacer 300 are disclosed in U.S. Pat. No. 5,330,459 issued Jul. 19, 1994 to LaVon et al.; U.S. Pat. No. 5,876,393 issued Mar. 2, 1999 to Ahr et al.; U.S. patent application Ser. No. 08/698,471, filed Aug. 15, 1996 in the name of Allen et al.; and U.S. Pat. No. 5,171,236 issued Dec. 15, 1992 to Dreier et al., which documents are incorporated herein by reference.

In embodiments where the expandable component 200 comprises a fecal void volume spacer 300, the topsheet 38 and the absorbent core 44 can comprise apertures 46 and 47 respectively (the aperture 46 is shown in phantom in FIG. 1). The apertures 46 and 47 can be registered with one another, as shown in FIG. 4, to provide a passageway for the communication of fecal material from the wearer's anal opening into the void space 311, but need not be configured as such. Aperture 46 may include any type of opening in the topsheet, including holes, slits and the like. Further, the aperture 46 may be partially or completely surrounded by an elastic means for holding the aperture 46 against the skin of the wearer or for holding the aperture 46 in a particular configuration.

As used herein, a "void space" is a cavity intermediate the topsheet 38 and the backsheet 42, which cavity is sized to accept fecal material. The void space preferably has a Z-direction height of at least about 0.65 centimeters (0.25 inch) and a volume of at least about 16.4 cubic centimeters (1.0 cubic inch). More preferably, the void space has a Z-direction height of at least about 1.5 cm and a volume of at least about 30 cubic centimeters. The volume of the void space 311 can be reduced if the absorbent core 44 is compressed between the topsheet 38 and the backsheet 42 by the wearer's weight. When expanded to the have the second thickness T2, the spacer 300 helps to maintain the volume of the void space 311 for receiving fecal matter.

The topsheet 38 and backsheet 42 are generally coextensive and at least partially peripherally joined together. As used herein the term "joined" refers to the condition where a first member or component is affixed or connected to a second member or component, either directly, or indirectly where the first member or component is affixed or connected to an intermediate member or component, which in turn is affixed or connected to the second member or component.

The topsheet 38 and backsheet 42 may be joined by any means well known in the art, such as adhesive bonding, heat sealing, ultrasonic bonding, or the like. Suitable adhesives for joining the topsheet 38 and backsheet 42 include Century 5227 adhesive manufactured by Century Adhesives, Inc. of Columbus, Ohio; HL1258 adhesive sold by the H. B. Fuller Company of St. Paul, Minn.; or Findley H2031 hot melt adhesive manufactured by the Findley Adhesive Company of Elmgrove, Wis. The adhesive can be applied in beads, bands, spirals, etc.

As used herein, the term "absorbent core " refers to any component of the diaper 20 used for absorbing and retaining body exudates. The absorbent core 44 may have opposed major faces and may, if desired, be encased by one or more layers of tissue. The absorbent core 44 may be made from a variety of commonly used materials such as comminuted wood pulp, typically referred to as airfelt. If desired, the absorbent core 44 may further contain absorbent gelling materials as is commonly used in the art. In particular, the absorbent core 44 may be made in accordance with the teachings of U.S. Pat. No. 4,610,678 issued Sep. 9, 1986 to Weisman et al.; U.S. Pat. No. 4,673,402 issued to Weisman et al. on Jun. 16, 1987; U.S. Pat. No. 4,834,735 issued May 30, 1989 to Alemany et al.; U.S. Pat. No. 5,147,345 issued Sep. 15, 1992 to Young et al.; U.S. Pat. Mo. 5,217,445 issued Jun. 8, 1993 to Cook et al.; and U.S. Pat. No. 5,234,423 issued Aug. 10, 1993 to Alemany et al., which patents are incorporated herein by reference for the purpose of showing how to make an absorbent core 44 suitable for use with the present invention. Absorbent gelling materials made in accordance with commonly assigned U.S. Pat. No. Re. 32,649 issued Apr. 19, 1988 to Brandt et al. are suitable for use in a diaper 20 according to the present invention.

The core 44 can be joined to the underside of the topsheet 38, as shown in FIG. 3. Alternatively, the core 44 can be joined to the backsheet 42, or the core 44 can comprise two or more layers. The absorbent core 44 may be adhesively joined to the topsheet 38 or backsheet 42 by any attachment means well known in the art. Suitable attachment means include but are not limited to adhesive beads and longitudinal and transverse bands or spirals of adhesive. Suitable adhesives for joining the core 44 to other components of the diaper 20 include XPO-9-035 adhesive manufactured by the Minnesota Mining and Manufacturing Company of St. Paul, Minn., as well as the Century 5227, the Fuller HL1258, and the Findley H2031 adhesives listed above.

Referring back to FIG. 1, the "topsheet" refers to any liquid pervious facing of the diaper 20 which contacts the skin of the wearer while the diaper 20 is worn and prevents substantial contact of the absorbent core 44 with the skin of the wearer. The topsheet 38 is preferably compliant, tactilely pleasant and non-irritating to the skin of the wearer. The topsheet 38 can be treated to be hydrophilic, to more readily transport body exudates to the absorbent core 44. Further, the topsheet 38 can have a lotion disposed thereon as described in U.S. Pat. Nos. 5,607,760; 5,643,588 and 5,968,025; each of which is incorporated by reference herein A suitable topsheet 38 may be manufactured from materials such as porous foams, apertured plastic films, natural fibers (e.g., wood fibers or cotton fibers), synthetic fibers (e.g., polyester or polypropylene fibers) or a combination of the foregoing. A particularly preferred topsheet 38 comprises polypropylene fibers having a denier of about 2.2 and a length of about 15.9 millimeters (0.62 inches). The topsheet 38 may be manufactured according to a number of techniques. For example, the topsheet 38 may be a nonwoven web of fibers spunbonded, carded, wet-laid, meltblown, hydroentangled, combinations of the above, or the like. One suitable topsheet 38 is carded and thermally bonded and has a basis weight of about 18 to about 25 grams per square meter. A suitable topsheet 38 is manufactured by the Veratec, Inc. Division of International Paper Company of Walpole, Mass. under the designation P-8.

The apertures 46 and 47 can be laterally centered on the longitudinal axis 36 or may be located in any other desirable location. Further, the apertures may be of any shape desired with a suitable shape being an oval having a longitudinal dimension, in one embodiment, of at least about 5.1 centimeters (2.0 inches) and a transverse dimension of at least about 3.8 centimeters (1.5 inches). The rearwardmost edge of the aperture 46 can be disposed at least about 15.2 centimeters (6.0 inches) from the rear edge 32B of the diaper 20 while it is worn. In one embodiment the rearwardmost edge of the aperture 46 is between about 17.8 centimeters (7.0 inches) and about 21.6 centimeters (8.5 inches) from the rear edge 32B of the diaper 20 while it is worn. Of course, the location, shape and size of the aperture 46 may be varied to accommodate different size wearers.

Aperture 47 is preferably at least partially registered with aperture 46, and can have a shape the same as, or similar to, the shape of aperture 46. Preferably, the spacer 300 is registered with the apertures 46 and 47, such that spacer 300 does not substantially obstruct aperture 46 or aperture 47, and such that at least a portion of each aperture 46 and 47 is disposed intermediate the longitudinally extending portions 322 of spacer 300. Alternatively, the spacer 300 can be joined to the body facing surface 39 of the topsheet 38.

The backsheet 42 is preferably impervious to fluids, such as urine, and prevents fluids absorbed by and contained in the absorbent core 44 from wetting undergarments, clothing and bedding. As used herein the term "backsheet" refers to any barrier disposed outwardly of the absorbent core 44 as the diaper 20 is worn and which contains absorbed liquids within the diaper 20. The backsheet 42 is preferably manufactured from a thin thermoplastic film, although other flexible liquid impervious materials may also be used. As used herein, the term "flexible" refers to materials which are compliant and will readily conform to the general shape and contours of the human body.

The backsheet 42 may comprise a woven or nonwoven material, polymeric films such as thermoplastic films of polyethylene or polypropylene, or composite materials such as film-coated nonwoven material. The backsheet 42 can be a thermoplastic film having a thickness of from about 0.01 millimeters to about 0.051 millimeters (0.0004 to 0.002 inches). If desired, the backsheet 42 may be embossed or matte finished to provide a clothlike appearance. A suitable material from which the backsheet 42 can be formed is a polyethylene film having a thickness of from about 0.010 mm to about 0.051 mm. Suitable polyethylene films are manufactured by Clopay Corp. of Cincinnati, Ohio under the designation P-18-1401, and by Tredegar Industries of Terre Haute, Ind. under the designations X8297 and HTS-5, FSII. Other suitable materials from which the backsheet 42 can be formed include RR8220 blown films and RR5475 cast films manufactured by Tredegar Industries. Other suitable backsheet materials can include breathable materials that permit vapors to escape from diaper 20 while still preventing exudates from passing through backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable materials are described in greater detail in PCT Application No. WO 95/16746, published lo on Jun. 22, 1995 in the name of E. I. DuPont, U.S. Pat. No. 5,865,823, issued on Feb. 2, 1999 in the name of Curro, and U.S. Pat. No. 5,571,096 issued to Dobrin et al. on Nov. 5, 1996. Each of these references is hereby incorporated by reference herein.

One or both of the topsheet 38 and the backsheet 42 can be extensible, being is formed of an elastomeric or stretchable film or comprising elastomeric elements such as elastomeric films, strands, or scrims as are known in the art. Extensible components are described in International Patent Publication WO 93/01785, "Stretchable Absorbent Articles" published Feb. 4, 1993, which document is incorporated herein by reference. Alternatively, the backsheet 42 or portions of the backsheet 42 may comprise a structural elastic-like film (SELF) web. A structural elastic-like film web is an extensible material that exhibits an elastic-like behavior in the direction of elongation without the use of added elastic materials. SELF webs suitable for the present invention are more completely described in commonly assigned U.S. Pat. No. 5,554,145 entitled "Absorbent Article with Multiple Zone Structural Elastic-Like Film Web Extensible Waist Feature" issued to Donald C. Roe, et al. on Sep. 10, 1996 and U.S. Pat. No. 5,518,801 entitled "Web Materials Exhibiting Elastic-Like Behavior", which issued to Chappell, et, al. on May 21, 1996 which are incorporated herein by reference.

Referring to FIGS. 3 and 4, the expandable component 200 preferably comprises a gas impermeable envelope 220 enclosing the compressed resilient element 215. The envelope 220 can be formed by positioning the resilient element 215 between two envelope walls 232 and 234, compressing the resilient element 215 between the walls 232 and 234, and joining the flexible envelope walls 232 and 234 to leave a cavity 236 therebetween for holding the resilient element 215.

The flexible walls 232 and 234 can be formed from two separate pieces of material, or alternatively, can be formed from a single piece of folded material. In FIGS. 3 and 4, the envelope 220 is integral with the backsheet 42, with the wall 234 comprising a portion of the backsheet 42, and with the wall 232 joined directly to a surface of the backsheet 42. Alternatively, the wall 234 can be formed from a piece of material separate from the backsheet 42, and the expandable component 200 can be joined directly to the backsheet 42 or any other component of the diaper.

The walls 232 and 234 of the envelope 220 are preferably substantially gas impermeable, and are preferably made from a material which is soft, flexible, and thermoformable. Suitable materials from which the walls 232 and 234 can be made include thermoplastic films, metallic foils, and laminates thereof. For instance, a suitable film is a polyethylene film having a thickness of from about 0.010 mm to about 0.051 mm. Suitable polyethylene films are manufactured by Clopay Corp. of Cincinnati, Ohio under the designation P-18-1401, and by Tredegar Industries of Terre Haute, Ind. under the designations X8297 and HTS-5, FSII. Other suitable materials from which the walls 232 and 234 can be formed include RR8220 blown films and RR5475 cast films manufactured by Tredegar Industries. Another suitable material from which one or both of the walls 232 and 234 can be made is a polyethylene film available from Tredegar Industries designated C-8323. Still other suitable materials for the walls 232 and 234 include a 3.0 mil nylon/LDPE/Surlyn coextruded film available as C735H-014 from Printpack, Inc., of Atlanta, Ga., and a 3.0 mil nylon/LLDPE coextruded film available as C733H-010 and C733-010, also available from Printpack, Inc.

With the resilient element 215 positioned between the walls 232 and 234, the walls 232 and 234 can be pressed together by a compressive force to compress the element 215, and while the element 215 is compressed, the walls 232 and 234 are joined at seams by any suitable joining method such as heat/pressure sealing, adhesive bonding, ultrasonic bonding, or the like, to prevent inflow of air to the cavity 236 upon release of the compressive force. Suitable seams can be formed by using Findley H2031 hot melt adhesive to join the perimeter of the wall 232 to the wall 234, which can comprise part of the backsheet 42. In one embodiment, the air between the walls 232 and 234 can be evacuated as the walls 232 and 234 are joined together, such as with vacuum sealing equipment known in the art, so that the pressure within the sealed envelope 220 is less than the surrounding outside atmospheric pressure.

In one embodiment, one or both of the walls 232 and 234 can be formed from an elastomeric or stretchable film to be extensible in order to accommodate expansion of the resilient element 215 once the envelope 220 is opened. For instance, one or both of the walls 232 and 234 can comprise a SELF web described in the copending, commonly assigned U.S. Pat. No. 5,554,145 issued Sep. 10, 1996 to Roe et al., which is incorporated herein by reference. Alternatively, one or both of the walls 232 and 234 can be pre-formed, such as by vacuum forming, embossing, or folding, to accommodate expansion of the resilient element 215. For instance, one or both of the walls 232 and 234 can have pleats for accommodating the expansion of the resilient element 215. In FIG. 3, the wall 232 is shown having longitudinally extending pleats 235. In yet another embodiment, the walls 232 and 234 can accommodate the expansion of the resilient element 215 if the unbonded portions of each of the walls 232 and 234 bounding the cavity 236 are sized to have a larger footprint than that of the resilient element 215, as described below.

Figure 11:
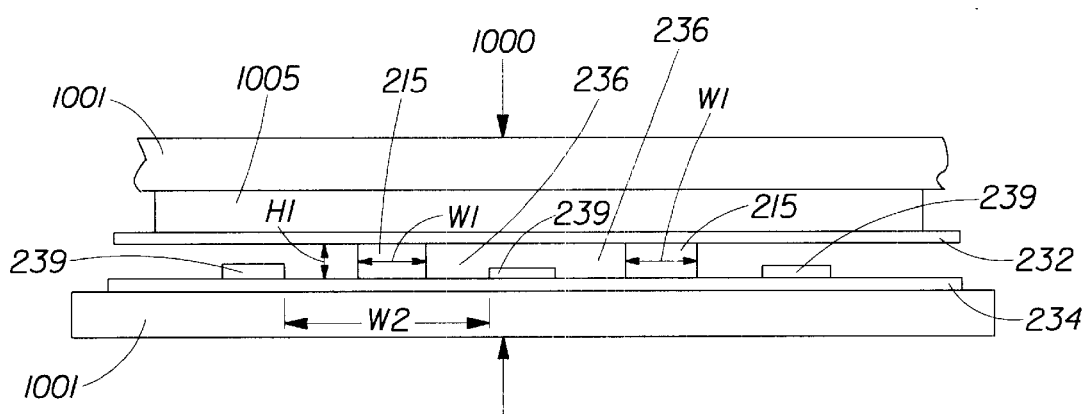
FIG. 11 is a schematic illustration of a method for forming an expandable component according to the present invention.

FIG. 11 is a schematic illustration of one apparatus for forming an expandable component 200. The walls 232, 234 and the resilient element 215 are shown positioned intermediate two pieces of plexiglas 1001. The resilient element 215 has a width W1, and a free, unrestrained thickness H1 prior to compression between walls 232 and 234. Portions of an adhesive layer 239 are spaced apart on wall 234 to leave portions of the walls 232 and 234 unbonded. The spacing W2 between portions of the adhesive layer 239 can be sized so that the unbonded portions of the walls 232 and 234 bounding the cavity 236 have a larger footprint than that of the resilient element 215. The walls 232 and 234 can thereby accommodate expansion of resilient element 215. For instance, the spacing W2 can be sized to be greater than or equal to the sum W1+H1 to accommodate expansion of the resilient element 215 to a thickness of about H1 upon opening of the envelope 220. Alternatively, the spacing W2 can be made smaller to restrict expansion of the resilient element 215 upon opening the envelope 220. A compressive loading 1000 presses the two walls 232 and 234 together. A conformable piece 1005 can be positioned between one of the pieces of plexiglas 1001 and the wall 232. The conformable piece 1005 aids in distributing the compressive load 1000 across the surface of the wall 232, removing air from between the walls 232 and 234, and reducing wrinkling of the wall 232 as the wall 232 is adhesively joined to the wall 234. The stiffness of the conformable piece 1005 in compression should be less than or about equal to the stiffness of the resilient element 215 in compression. The conformable piece 1005 can be formed from the same or different material from which resilient element 215 is formed, and can have a thickness greater than or equal to the thickness H1 of the resilient element 215.

Figure 5:
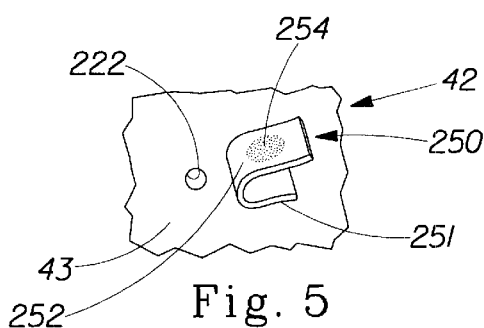
FIG. 5 is an enlarged view of a portion of the port in the air impermeable envelope, and the releasable closure for covering the port.

Referring to FIG. 5, the gas impermeable envelope 220 can comprise a port 222 in one of the walls 232, 234, and a releasable closure 250 covering the port. The releasable closure 250 may include a piece of film 251 or other material joined to or integral with the wall through which the port 222 extends. The releasable closure 250 can be formed from the same material from which the walls 232 and 234 are formed or a different material, and can be joined to the envelope 220 by any suitable method, including but not limited to adhesive bonding, mechanical bonding, ultrasonic bonding, heat sealing, and the like. The releasable closure 250 may be partially or completely peeled from the envelope 220 to expose the port 222, thereby permitting air to enter the cavity 236 for providing expansion of resilient element 215 within the cavity 236. The size of the port 222 can be varied to vary the rate at which the resilient element 215 expands once the releasable closure 250 is opened. In general, the resilient element 215 will expand more rapidly as the size of the port 222 is increased.

The releasable closure 250 can have adhesive 252 disposed thereon for adhering the film 251 to the wall through which the port 222 extends. The adhesive 252 can also permit the closure 250 to be resealed, to thereby cover the port 222 and prevent the escape of air drawn into the cavity 236 by expansion of the resilient element 215. Suitable pressure sensitive adhesives for use with the releasable closure 250 include Century Adhesive A-305-IV manufactured by the century adhesives Corporation of Columbus, Ohio; Adhesive Number 34-2823 manufactured by the National Starch and Chemical Company of Bridgewater, N.J.; and Fuller adhesive numbers HL-2238-XZP and HL-2254-XZP manufactured by the H. B. Fuller Company of Vadnais Heights, Minn. In an alternative embodiment, a first material can surround the port 222, and the releasable closure 250 can include a second material which is cohesive with the first material. In another embodiment, the closure 250 can comprise a piece of cellophane tape, such as Scotch Brand Model 600 transparent tape manufactured by the 3M company of Minneapolis, Min.

Figure 5A:
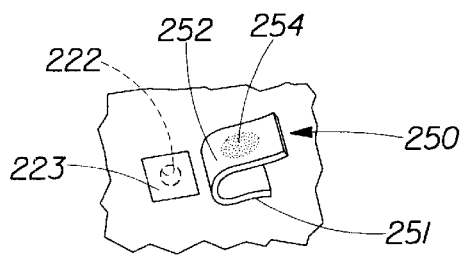
FIG. 5A is an alternative embodiment of the portion of the present invention shown in FIG. 5.
Figure 6:
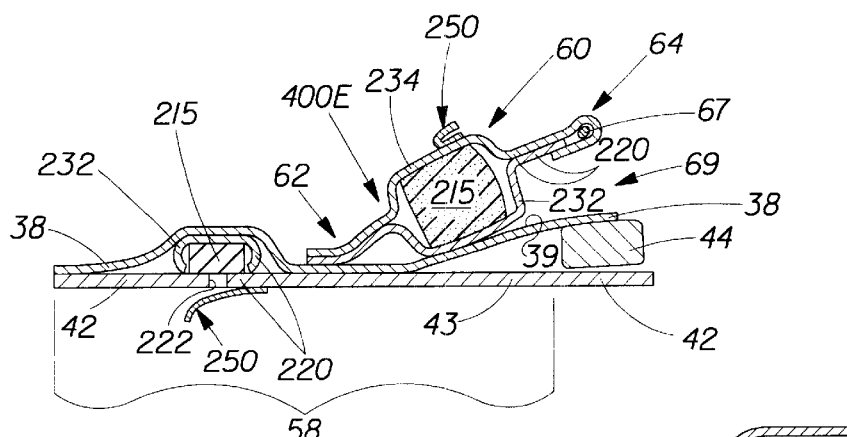
FIG. 6 is a sectional view taken along lines 6—6 in FIG. 2 showing expandable components disposed in the side margin of the diaper, including an expandable component disposed on a leg cuff.
Figure 6A:
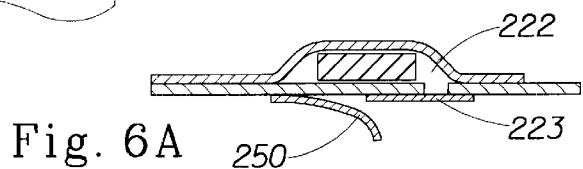
FIG. 6A is an alternative embodiment of the portion of the present invention shown in FIG. 6.

In certain preferred embodiments, as shown in FIGS. 5A and 6A, the port 222 may comprise a gas-permeable component 223 such as a gas-permeable membrane or film. The rate of expansion of the resilient element 215, or other expandable component, may be controlled by varying the gas diffusion coefficient of the gas-permeable component 223 or varying the port 222 area. Suitable gas-permeable components include films and other materials having MVTR values of between about 1500 and about 3700 grams water vapor per 100 square meters per 24 hour period measured by the test method described below. For example, the gas-permeable component may comprise microporous films, monolithic films, nonwovens, wovens, foams, adhesives or any combination of these materials which meet the parameters stated herein. Films suitable for use as the gas-permeable component include microporous films such as 201-1999 and BR106 available from Clopay Corp. of Cincinnati, Ohio.

The MVTR of a sample is measured as follows: a known amount of CaCl.sub.2 is put into a flanged cup. A sample material is placed on top of the cup and held securely by a retaining ring and gasket. The assembly is then weighed and recorded as the initial weight. The assembly is placed in a constant temperature (40.degree. C.) and humidity (75% RH) chamber for five (5) hours. The assembly is then removed from the chamber and allowed to equilibrate for at least 30 minutes at the temperature of the room where the balance is located. The assembly is then weighed and recorded as the final weight. The mass vapor transmission rate (MVTR) is calculated and expressed in g/m.sup.2/24 hr. using the following formula:

$$\text{MVTR} = \frac{(\text{final weight} - \text{initial weight}) \times 24.0}{\text{area of sample in meters} \times 5.0 \text{ (time in chamber)}}$$

As noted above, it has been found that the rate of expansion of the expandable member can be controlled by changing the area of the port or the gas diffusion coefficient or rate of the gas-permeable component covering the port. For example, decreasing either the area of the port 222 or decreasing the gas diffusion coefficient, or rate, of the gas-permeable component covering the port 222, will generally result in a decreased expansion rate for the expandable component and an increase in such variable will generally increase the rate of expansion. This ability to control the rate of expansion of the expandable component is important to the functionality of the present invention. In some circumstances, if the expandable component 200 expands too rapidly, the product may be too bulky to facilitate the easy application of the wearer's clothing over the product. However, in these and other situations, if the expandable component 200 expands too slowly, it may fail to perform its intended function. For example, if the expandable component 200 is a spacer designed to provide void volume to hold feces, an expansion rate which is too slow may result in the spacer being fully expanded and thus fully functional only after a defecation occurs. Accordingly, it is preferred that the diaper be designed to permit the expansion of the expandable member 200 quickly enough to perform the intended function, but slowly enough to allow easy application of the article. Thus, it is preferred that the expandable component expand to about 90% of its original capacity in less than about 20 minutes from the time at which the expandable component is activated. Also, it is preferred that the expandable component expand to about 90% of its original capacity only after at least 5 minutes from the time at which the expandable component is activated. In other preferred embodiments, the expandable component expands to about 90% of its original capacity within between about 6 minutes and about 15 minutes of activation.

In one suitable embodiment, the port 222 comprises two 12 mm diameter holes (i.e., port 222 area=226 mm$^2$) covered by the above-referenced gas permeable Clopay 201-1999 film. Such a construction has been found to provide for expansion to about 90% of the original, unconstrained thickness of the resilient material within about 6 minutes when the resilient material is a porous, open-celled foam, as described below. Reducing the port 222 to one 12 mm diameter hole (i.e., reducing the port area to 113 mm$^2$) will approximately triple the time required for the resilient element to expand to 90% of its original thickness.

In any case, the gas-permeable component may be affixed over the port 222 by any known bonding means including, but not limited to, adhesive bonding, mechanical bonding, ultrasonic bonding or any combination of these or other bonding means. In one preferred embodiment, the gas permeable component is affixed over the port by bonding the gas-permeable component to the gas impermeable envelope 220 around the periphery of the port 222.

In another embodiment, the envelope 220 can be formed without a port 222. The closure 250 can include a relatively low tack adhesive 252, and a relatively high tack adhesive 254, as shown in FIG. 5. Upon peeling the closure 250 from the envelope 220, the high tack adhesive 254 tears the envelope wall and creates an opening in the envelope 220 through which air can enter. In yet another embodiment, the port 222 and the releasable closure 250 can be omitted, and the air impermeable envelope 220 can be opened by tearing the walls 232 and 234 apart manually, by cutting the envelope 220 with a pair of scissors, or by otherwise piercing the envelope 220.

The resilient compressed element 215 is preferably porous, so that when the releasable closure 250 is removed from the port 222, expansion of the resilient element 215 draws air into the resilient element 215, as well as into the space in the cavity 236 not occupied by the resilient element 215. In one such embodiment, the resilient element can comprise a porous sponge. In another embodiment, the resilient element 215 can comprise an open celled foam, such as an open celled polymeric foam. By open celled it is meant that the individual cells of the foam are for the most part not completely isolated from each other by the polymeric material of the cell walls. Open celled foams, can also include foams which are initially closed celled, and which are reticulated, such as by compression, to form an open celled structure within the envelope 220.

One suitable porous foam from which the resilient element 215 can be made is polyurethane foam, such as is available as #1230 foam from the American Excelsior Corp. of Cincinnati, Ohio. Another suitable porous, open celled foam is a foam prepared by polymerizing a high internal phase emulsion, such as is described in U.S. Pat. No. 5,147,345; High Efficiency Absorbent Articles for Incontinence Management, issued Sep. 15, 1992 in the name of Young et al., which patent is incorporated herein by reference. The pore volume of the resilient element 215 can be any suitable value. In one embodiment, the pore value is at least about 2 ml/gram, and preferably between about 2 and about 100 ml/gram prior to compression in the envelope 220, as measured in the above referenced U.S. Pat. No. 5,147,345. The pore volume is a measure of the volume of the open cells in the porous foam structure per unit mass of the solid material which forms the foam structure. Pore volume influences the flexibility and the compression deflection characteristics of the resilient element 215. For a given material, as pore volume increases, flexibility increases and resistance to compression generally decreases. In addition, as pore volume increases, the amount of air per unit weight of the resilient element 215 which can be drawn into the envelope 220 as the resilient element 215 expands generally also increases. Accordingly, increased Z-direction thickness can be obtained with a relatively small amount and weight of material.

The resilient element 215 can have any cell size, however a cell size of at least about 5 microns prior to compression in the envelope 220, as measured in U.S. Pat. No. 5,147,345 is preferred. For a given material, the rate at which the resilient element 215 is expands will generally increase as the cell size of the resilient element 215 increases.

The resilient element 215 preferably has a density prior to compression in envelope 220 of less than about 1.0 gram per cubic centimeter, and more preferably between about 0.01 and about 0.50 gram per cubic centimeter, as measured in the above referenced U.S. Pat. No. 5,147,345. The density of the resilient element 215 can also influence the flexibility and compression deflection characteristics of the resilient element. In general, for a given material, as the density of the resilient element 215 decreases, the flexibility increases and the resistance to compression decreases.

By way of example, a spacer 300 was formed using layers of a porous open celled foam having a density of about 0.03 gm/cc, a pore volume of about 32 ml/gram, and a cell size of between about 50 and about 75 microns. The foam was made according to the teachings of above referenced U.S. Pat. No. 5,147,345, with a monomer composition similar to that provided in Example 6 of U.S. Pat. No. 5,147,345. The resilient element 215 comprised seven layers of the porous open celled foam, each layer having a closed shape enclosing an open area, and each layer having a shape generally the same as the shape of the other layers. Each layer had a width W1 (FIG. 11) of about 12.7 mm (0.5 inch) as measured around the perimeter of the closed shape, and a surface area of about 30 square centimeters, with each layer enclosing an open area of about 30 square centimeters. Each layer of foam had a free, unrestrained thickness of about 0.070 inch, so that the resilient element 215 had a total Z-direction thickness Hi of about 0.49 inch prior to compression. Findley H2031 adhesive was applied to one side of a first sheet of polyethylene, the sheet of polyethylene having a thickness of about 0.0010 inch (0.025 mm). The adhesive was applied to the sheet of polyethylene so as to leave an adhesive free area having a closed shape. The adhesive free area was sized to have a projected area larger than that of the layers forming the resilient element 215, to thereby accommodate expansion of the resilient element 215. The width W2 (Figure 11) of the adhesive free area at any point around the perimeter of the adhesive free area was about 2.54 centimeters (1.0 inch), or about equal to the height H1 plus the width W1. A port 222 having a diameter of about 0.5 inch was cut in the first sheet of polyethylene, and covered with a piece of Scotch Brand Model 600 Transparent Tape on the side of the first sheet of polyethylene to which adhesive was not applied.

The seven layers of foam were then placed between the first sheet of polyethylene and a second sheet of polyethylene. The seven layers of foam where compressed by pressing the two sheets of polyethylene and the seven layers of foam together between two pieces of plexiglas, as shown in FIG. 11. The compressive loading was about 28 psi. While maintaining the compressive loading, the edges of the first and second sheets of polyethylene were pressed together to adhesively join the sheets around the perimeter of the spacer to provide an air impermeable envelope 220.

The caliper of the spacer, including the thickness of both sheets of polyethylene and the seven layers of compressed foam was about 0.150 inch. The piece of Transparent Tape was then removed from the port 222, and the Z-direction caliper of the spacer was measured at predetermined time intervals. The Z-direction caliper was measured using a dial indicator, and was measured under a confining pressure of about 0.24 psi with the confining pressure applied to the spacer with a load foot having a 1.0 square inch surface area. The spacer had the following Z-direction calipers at the following times after removing the tape from the port in the first polyethylene sheet:

| TIME AFTER OPENING | CALIPER |
|---|---|
| 0 seconds | 0.150 inch |
| 5 seconds | 0.175 inch |
| 10 seconds | 0.190 inch |
| 30 seconds | 0.255 inch |
| 45 seconds | 0.290 inch |
| 2 minutes | 0.402 inch |
| 5 minutes | 0.460 inch |

In embodiments comprising a gas permeable component (i.e. a microporous breathable film) affixed over the entire port 222, the rate of expansion may be closely controlled by varying the port area and the permeability of the gas permeable element as measured by Moisture-Vapor Transmission Rate, or MVTR. The table below shows the expansion rate, as measured by the time required for the resilient element to expand to 90% of its original unconstrained thickness for a variety of combinations of port size, permeability of the gas permeable element, and the compressive resistance of the resilient element. The resilient elements in the examples are open celled microporous absorbent foams produced according to aforementioned U.S. Pat. No. 5,147, 345. The "soft" variant of the foam experiences a compression of about 41% (i.e., the foam has a thickness under said pressure equal to about 59% of its original, unconstrained thickness) under a 1.0 psi applied pressure, while the "stiff" variant of the foam will compress about 6% under the same applied pressure.

TABLE 1

| Resilient Element | Total Port Area (mm$^2$) | Gas Permeability of Gas Permeable Element (g/100 m$^2$/24 hr) | Time for Resilient Element to Expand to 90% of Original Thickness (min) |
| --- | --- | --- | --- |
| stiff foam | 113 | 1500 | >30 |
| stiff foam | 113 | 3700 | 17–20 |
| soft foam | 226 | 3700 | 6–7 |
| stiff foam | 226 | 3700 | 6 |

Referring to FIGS. 1–4 and 6, the expandable component 200 can also comprise a seal 400 for reducing leakage of body exudates from between the absorbent article and the wearer's skin. Such seals 400 can include waist region seals 400A and 400B positioned in the front and rear waist regions 22 and 24, respectively, and side margin seals 400C and 400D positioned in the side margins 58. Each of the seals 400 comprises a compressed resilient element 215 disposed within an air impermeable envelope 220. The waist region seals 400A, B can each have a generally laterally extending resilient element 215, and the side margin seals 400C, D can each have a generally longitudinally extending resilient element 215. The resilient elements 215 can be disposed intermediate the top sheet 38 and the backsheet 42, as shown in FIGS. 3 and 4. Referring to FIGS. 3, 4, and 6, the seals 400 expand from a first thickness to a second thickness greater than the first thickness upon opening the envelope 220 enclosing the resilient element 215.

Referring to FIGS. 2 and 6, the diaper 20 can also include side margin seals 400E, wherein each side margin seal 400E is associated with a barrier leg cuff 60. Each barrier leg cuff 60 extends generally longitudinally along a side margin 58 of the diaper 20. Each leg cuff 60 has proximal edge 62 joined to an underlying portion of the diaper 20 in the side margin 58, and distal edge 64 spaced from the proximal edge 62. The distal edge 64 can include a spacing element 67, such as an elastic element, for spacing the distal edge 64 from the body facing surface 39 of the topsheet 38.

The barrier cuff 60 according to the present invention may include a resilient element 215 disposed within an air impermeable envelope 220. The air impermeable envelope 220 can comprise a first flexible wall 232 and a second flexible wall 234. Each of the walls 232 and 234 can comprise a plastic film, such as a polyethylene film. The walls 232 and 234 can be joined together along the lengths of the proximal and distal edges 62 and 64, as well as at the ends of the barrier leg cuffs positioned in the front and rear waist regions 22 and 24. In the embodiment shown in FIG. 6, the wall 232 is joined to the topsheet 38 at the proximal edge 62. The wall 232 can be joined to the topsheet 38 by any suitable means, including but not limited to adhesive, ultra-sonic, mechanical, or heat bonding. The wall 234 is preferably folded to form a hem for containing the spacing element 67, and is joined to the wall 232 along the distal edge 64.

The wall 234 can include a port 222 covered by a releasable closure 250. Upon release of the closure 250, the resilient element 215 expands from a compressed configuration. Expansion of the resilient element 215 provides a seal between the diaper 20 and the wearer's skin. Expansion of the resilient element 215 also helps to space the distal edge 64 from the topsheet 38, and thereby forms a channel 69 intermediate the carrier leg cuff 60 and the topsheet 38. The channel 69 holds liquid and solid body exudates which could otherwise leak from between the side margin 58 and the wearer's skin. FIG. 6 shows a barrier cuff 60 having both a spacing element 67 and an expandable seal 400E. Alternatively, the spacing element 67 could be omitted. In embodiments where the spacing element 67 is omitted, the seal 400E can be positioned at the distal edge 64 of the barrier cuff 60.

Figure 7:
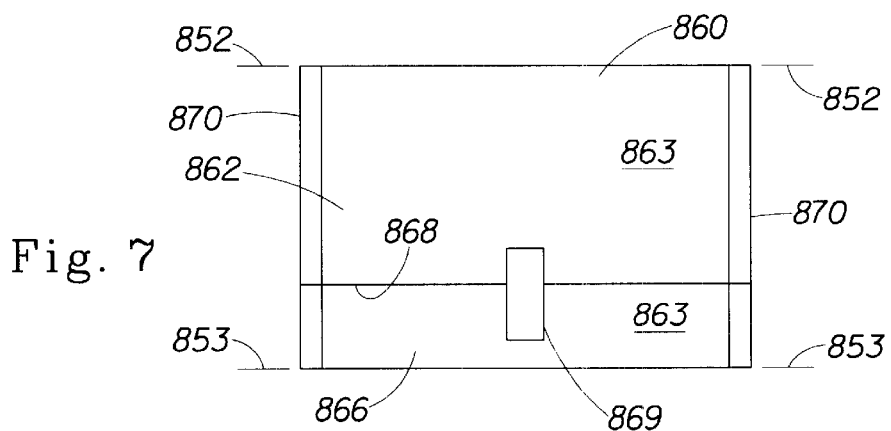
FIG. 7 is a frontal view of an individually wrapped and folded sanitary napkin.
Figure 8:
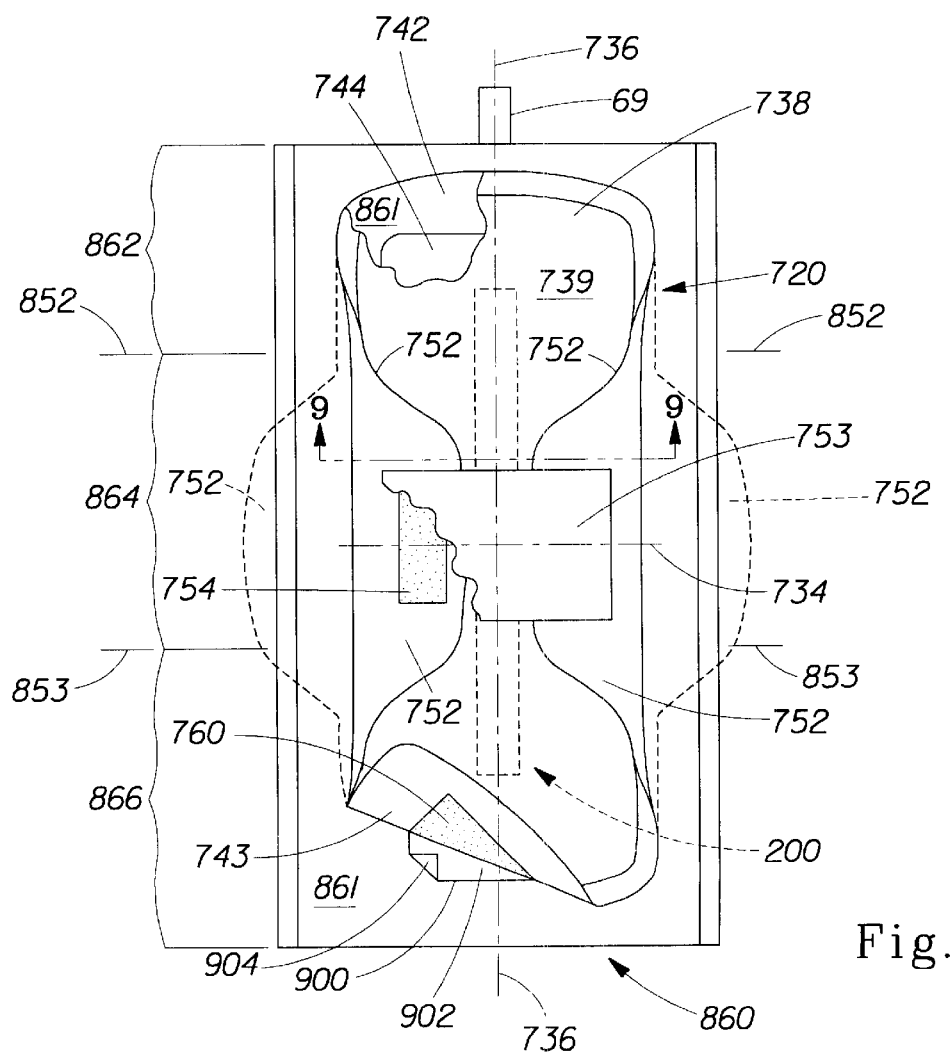
FIG. 8 is a top view of the individually wrapped sanitary napkin of FIG. 7, shown unfolded, and having an expandable component (shown in phantom) extending along the longitudinal centerline of the sanitary napkin.

FIGS. 7–10 illustrates a sanitary napkin 720 according to the present invention. FIGS. 7 and 8 show an individually packaged sanitary napkin 720 packaged in a flexible wrapper 860. The flexible wrapper 860 has an interior surface 861 and an exterior surface 863. The sanitary napkin 720 may be joined to the interior surface 861 and folded as a unit with the flexible wrapper 860 along two spaced apart fold lines 852 and 853. The fold lines 852 and 853 divide the flexible wrapper 860 into three panels 862, 864, and 866. The wrapper 860 and the sanitary napkin 720 are shown in a closed, folded configuration in FIG. 7, and in a fully unfolded configuration in FIG. 8.

The wrapper 860 protects the sanitary napkin 20 from becoming soiled prior to use. The flexible wrapper 860 can be formed from various materials including but not limited to paper, thermoplastic films, metallic foils, or laminates thereof. A suitable material from which the flexible wrapper 860 can be formed comprises a polyethylene film having a thickness of about 0.025 millimeter (about 1 mil). The folded wrapper 860 can be sealed along package edges 870, such as by thermally or adhesively bonding two or more of the panels 862–866 together. A flap edge 868 of the panel 862 can be joined to underlying panel 866 by a piece of tape 869.

The sanitary napkin 720 has a longitudinal centerline 736 and a lateral centerline 734. The sanitary napkin 720 comprises a liquid pervious topsheet 738 having a body facing surface 739, a liquid impervious backsheet 742 joined with the topsheet 738 and having a garment facing surface 743, and an absorbent core 744 positioned intermediate the topsheet 738 and the backsheet 742.

Figure 9:
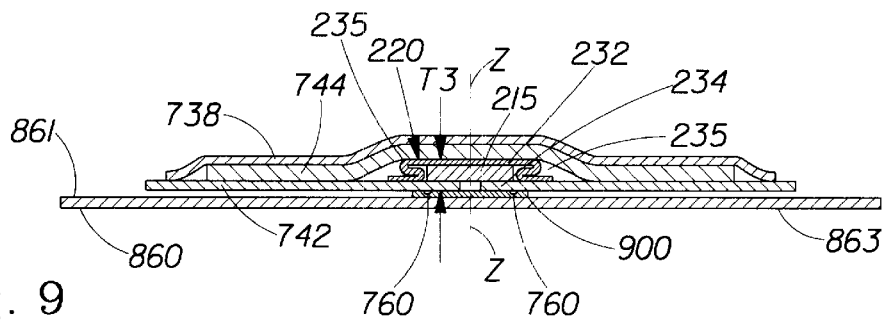
FIG. 9 is a sectional view taken along lines 9—9 of FIG. 8 showing the expandable component in a compressed configuration.
Figure 10:
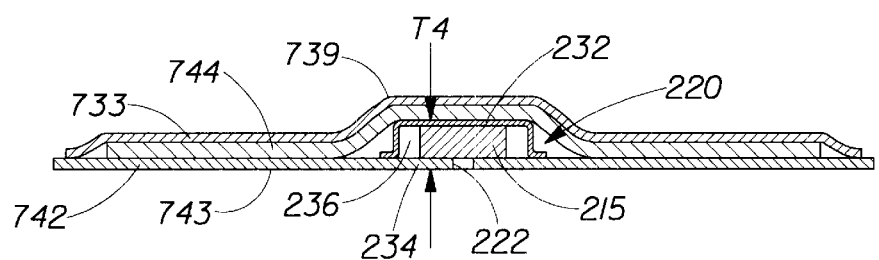
FIG. 10 is a sectional view similar to that of FIG. 9 showing the expandable component in an expanded configuration.

The sanitary napkin 720 further comprises an expandable component 200 (shown in phantom in FIG. 8). The expandable component 200 includes a compressed resilient element 215 disposed in a gas impermeable envelope 220, as shown in FIGS. 9 and 10. the expandable component 200 expands from a compressed configuration having a first Z-direction thickness T3, to an expanded configuration having a second Z-direction thickness T4 greater than the first thickness T3, upon opening of the air impermeable envelope 220. The second thickness T4 is preferably at least about twice the first thickness T3. The expandable component 200 thereby locally increases the Z-direction caliper of the sanitary napkin 720. The compressed and expanded configurations are shown in FIGS. 9 and 10, respectively. In the expanded configuration, the expandable component 200 provides conformance of a portion of the sanitary napkin 720 with the wearer's body to enhance acquisition of body exudates and reduce soiling of the wearer's undergarment.

While the topsheet 738, backsheet 742, and absorbent core 744 may be assembled in a variety of well known configurations, suitable configurations are described generally in U.S. Pat. No. 5,007,906 issued Apr. 16, 1991 to Osborn et al.; U.S. Pat. No. 4,950,264 issued to Osborn on Aug. 21, 1990; U.S. Pat. No. 4,425,130 issued to DesMarais on Jan. 10, 1984; U.S. Pat. No. 4,321,924 issued to Ahr on Mar. 30, 1982; and U.S. Pa. No. 4,589,876 issued to Van Tilburg on Aug. 18, 1987. Each of these patents is incorporated by reference for the purpose of generally describing the assembly of the components of a sanitary napkin 720.

The topsheet 738 is liquid pervious permitting liquids to readily penetrate through its thickness. A suitable topsheet 738 may be manufactured from a wide range of materials such as woven and nonwoven materials, polymeric materials such as apertured formed thermoplastic films; and thermoplastic scrims. A suitable topsheet 738 comprises an apertured formed film. Suitable formed films are described in U.S. Pat. No. 3,929,135 issued to Thompson on Dec. 30, 1975; U.S. Pat. No. 4,324,246 issued to Mullane et al. on Apr. 13, 1982; U.S. Pat. No. 4,342,314 issued to Radel et al. on Aug. 3, 1982; U.S. Pat. No. 4,463,045 issued to Ahr on Jul. 31, 1984; and U.S. Pat. No. 5,006,394 issued to Baird on Apr. 9, 1991. Each of these patents is incorporated herein by reference. A suitable formed film topsheet 738 is marketed on sanitary napkins by The Procter and Gamble Company of Cincinnati, Ohio as DRI-WEAVE. The body facing surface 739 of the topsheet 738 can be hydrophilic to enhance transfer of body fluids through the topsheet 738. A surfactant can be incorporated into the polymeric materials of the formed film topsheet, or alternatively, the body facing surface 739 of the topsheet can be treated with a surfactant as described in above referenced U.S. Pat. No. 4,950,254 to Osborn.

The backsheet 742 is impervious to liquids and can be manufactured from a thin plastic film, although other flexible liquid impervious materials may be used. A suitable backsheet 742 is made from a polyethylene film having a thickness of from about 0.010 mm to about 0.051 mm. Suitable films from which the backsheet 742 can be formed are manufactured by Clopay Corporation of Cincinnati, Ohio under the designation P18-0401 and by Ethyl Corporation, Visqueen Division, of Terre Haute, Ind. under the designation XP-39385.

Alternatively, one or both of the topsheet 738 and the backsheet 742 can be extensible, being formed of an elastomeric or stretchable film. For example, the backsheet 742 or portions of the backsheet 742 may comprise a structural elastic-like film (SELF) web described above. SELF webs suitable for the present invention are more completely described in commonly assigned U.S. Pat. Nos. 5,554,145 and 5,518,801, which are incorporated herein by reference.

The absorbent core 744 can be any absorbent means which is capable of absorbing or retaining liquids (e.g., menses and/or urine). The absorbent core may be manufactured in a wide variety of sizes and shapes (e.g., rectangular, oval, hourglass, etc.) and from a wide variety of liquid-absorbent materials such as comminuted wood pulp, which is generally referred to as airfelt. Other suitable absorbent materials include creped cellulose wadding; meltblown polymers; chemically stiffened, modified, or cross-linked cellulosic fibers; tissue including tissue wraps and tissue laminates; absorbent foams; absorbent sponges; superabsorbent polymers; absorbent gelling materials, and combinations of the above. Suitable absorbent structures for use as the absorbent core 744 of the present invention are described in U.S. Pat. No. 5,007,906 issued Apr. 16, 1991 to Osborn; U.S. Pat. No. 4,950,264 issued Aug. 21, 1990 to Osborn; U.S. Pat. No. 4,610,678 issued Sep. 9, 1986 to Weisman et al.; U.S. Pat. No. 4,834,735 issued May 30, 1989 to Alemany et al.; and European Patent Application No. 0 198 683 published Oct. 22, 1986 in the name of Duenk, et al. Each of these patents is incorporated herein by reference for the purpose of showing suitable constructions and materials for the absorbent core 744.

The sanitary napkin 720 can also include a pair of laterally extending flaps 752. The flaps 752 are configured to drape over the edges of the wearer's panty in the crotch region so that the flaps 752 are disposed between the edges of the wearer's panty and the thighs. The flaps 752 help prevent soiling of the wearer's body and panties by body exudates. The flaps 752 can have flap adhesive 754 for fastening the flap 752 to the wearer's panty to thereby keep the sanitary napkin 720 properly positioned in the panty. A piece of flap release paper 753 engages the flap adhesive 754 on each flap 752 to hold the flaps 752 in a folded position overlying the topsheet 738 while the sanitary napkin 720 is folded inside the wrapper 860. The flaps 752 can be unfolded (as shown in phantom in FIG. 8) once the release paper 753 is peeled from the adhesive 754. The following U.S. Patents are incorporated herein by reference for the purpose of showing sanitary napkin constructions having flaps 752: U.S. Pat. No. 4,950,264 issued Aug. 21, 1990 to Osborn; U.S. Pat. No. 4,589,876 issued May 20, 1986 to Van Tilburg; U.S. Pat. No. 4,608,047 issued Aug. 26, 1986 to Mattingly; U.S. Pat. No. 4,687,478 issued Aug. 18, 1987 to Van Tilburg; and U.S. Pat. No. 5,007,906 issued Apr. 16, 1991 to Osborn et al. The flaps 752 are omitted in FIGS. 9 and 10 for clarity.

The sanitary napkin 720 can also include garment attachment adhesive 760 (FIG. 8) for joining the garment facing surface 743 of the backsheet 742 to the wearer's panties. A strip of wrapper release paper 900 covers the garment attachment adhesive 760 until the wearer is ready to fasten the sanitary napkin to the wearer's undergarment. The strip of release paper 900 has a first surface 902 and an oppositely facing surface 904. The first surface 902 is joined to the garment facing surface 743 of the backsheet 742 by the garment attachment adhesive 760, and the second surface 904 of the release paper 900 is joined to the interior surface 861 of the flexible wrapper 860 by wrapper adhesive. The first surface 902 is preferably treated, such as with a coating comprising silicon, so that the adhesive bond between the surface 902 and the backsheet 742 has a lower strength than the adhesive bond between the surface 904 and the flexible wrapper 860. Such a difference is desirable so that the release paper 900 stays joined to the wrapper 860 when the consumer separates the sanitary napkin 720 from the wrapper 860. The garment attachment adhesive 760 can comprise a pressure sensitive adhesive. Suitable adhesives include Century Adhesive A-305-IV manufactured by the century adhesives Corporation of Columbus, Ohio; Adhesive Number 34-2823 manufactured by the National Starch and Chemical Company of Bridgewater, N.J.; and Fuller adhesive numbers HL-2238-XZP and HL-2254-XZP manufactured by the H. B. Fuller Company of Vadnais Heights, Minn. Suitable release paper 900 is described in U.S. Pat. No. 4,917,697, which patent is incorporated by reference.

Suitable release paper 900 is manufactured by Akrosil Corporation of Menasha, Wis. as BL30MG-A Silox E1/O and BL30MG-A Silox 4P/O.

Referring to FIGS. 9 and 10, the expandable component 200 comprises a compressed resilient element 215 enclosed in a gas impermeable envelope 220 having two envelope walls 232 and 234. In FIGS. 9 and 10, the envelope 220 is integral with the backsheet 742, with the wall 234 comprising a portion of the backsheet 742, and with the wall 232 joined directly to a surface of the backsheet 742. Alternatively, the wall 234 can be formed from a piece of material separate from the backsheet 742.

The walls 232 and 234 of the envelope 220 are gas impermeable, and are preferably made from a material which is soft and flexible. Suitable materials from which the walls 232 and 234 can be made include thermoplastic films. For instance, a suitable film is a polyethylene film having a thickness of from about 0.010 mm to about 0.051 mm. Suitable polyethylene films are manufactured by Clopay Corp. of Cincinnati, Ohio under the designation P-18-1401, and by Tredegar Industries of Terre Haute, Ind. under the designations X8297 and HTS-5, FSII. Other suitable materials from which the walls 232 and 234 can be formed include RR8220 blown films and RR5475 cast films manufactured by Tredegar Industries.

In one embodiment, one or both of the walls 232 and 234 can be formed from an elastomeric or stretchable film to accommodate expansion of the resilient element 215. For instance, one or both of the walls 232 and 234 can comprise a SELF web described in U.S. Pat. No. 5,518,801, which application is incorporated herein by reference. Alternatively, one or both of the walls 232 and 234 can be pre-formed, such as by vacuum forming, embossing, or folding, to accommodate expansion of the resilient element 215. For instance, one or both of the walls 232 and 234 can have pleats for accommodating the expansion of the resilient element 215. In FIG. 9, the wall 232 is shown having longitudinally extending pleats 235.

Referring to FIGS. 9 and 10, the gas impermeable envelope can comprise a port 222 in the portion of the backsheet 742 to which the wrapper release paper 900 is adhesively joined. The port 222 preferably comprises a gas-permeable component as described above which helps control the rate of expansion of the expandable component 200. As shown in FIG. 9, the release paper 900 covers the port 222, and prevents air from entering the cavity 236 between the wall 232 and the wall 234. The release paper 900 and the garment attachment adhesive 760 form a releasable closure for covering the port 222. When the consumer removes the flexible wrapper 860 from the sanitary napkin 720, the release paper 900 remains adhered to the wrapper 860. The port 222 is thereby uncovered, permitting expansion of the compressed resilient element 215 within the cavity 236, as shown in FIG. 10. In alternate embodiments, the envelope 220 can comprise a resealable releasable closure covering the port 222. In yet another embodiment, the port 222 can be omitted, and the air impermeable envelope 220 can be opened by tearing the walls 232 and 234 apart manually, by cutting the envelope 220 with a pair of scissors, or by otherwise piercing the envelope 220.

The resilient compressed element 215 is preferably porous, so that when the releasable closure 250 is removed from the port 222, expansion of the resilient element 215 draws air into the resilient element 215, as well as into the space in the cavity 236 not occupied by the resilient element 215. In one such embodiment, the resilient element can comprise a porous sponge. In another embodiment, the resilient element 215 can comprise an open celled foam, such as an open celled polymeric foam. One suitable porous foam from which the resilient element 215 can be made is polyurethane foam, such as is available as #1230 foam from the American Excelsior Corp. of Cincinnati, Ohio. Another suitable porous, open celled foam is a foam prepared by polymerizing a high internal phase emulsion, such as is described in above referenced U.S. Pat. No. 5,147,345; High Efficiency Absorbent Articles for Incontinence Management, issued Sep. 15, 1992 in the name of Young et al.

The expandable component 200 can be disposed intermediate the backsheet 742 and the topsheet 738. In FIGS. 9 and 10 the compressed resilient element 215 is positioned intermediate the backsheet 742 and the absorbent core 744. The compressed resilient element 215 thereby provides displacement of a portion of the topsheet 738 and the absorbent core 744 relative to the backsheet 742 for enhanced acquisition of body exudates. The compressed resilient element 215 can extend along the longitudinal centerline 736, as shown in phantom in FIG. 8. The resilient element 215 thereby convexly shapes a portion of the body facing surface 739 along the longitudinal centerline 736, and increases the Z-direction thickness of the sanitary napkin 720 along the longitudinal centerline to help conform the topsheet 738 to the wearer's body, particularly in the labial, perianal, and gluteal groove areas. In one embodiment the resilient element 215 can have a lateral width of between about 1.0 to about 2.0 centimeters and a free, unrestrained Z-direction thickness of between about 1.0 and about 2.0 centimeters prior to compression. In another embodiment, the Z-direction thickness of the resilient element 215 can vary along the longitudinal centerline 736, thereby providing variations in displacement of the topsheet 738 and core 744 along the length of the sanitary napkin 720 for selective fit in the labial, perianal, and gluteal groove areas of the body.

Only one longitudinally extending resilient element 215 is shown in FIGS. 8–10. However, in other embodiments, the sanitary napkin can include multiple resilient elements 215. The resilient elements 215 can be disposed in separate or interconnected air impermeable envelopes 220. In the embodiment shown in FIGS. 9–10, the resilient element 215 is disposed intermediate the backsheet 742 and the topsheet 738. In yet another embodiment, the expandable component can be joined to the garment facing surface 743 of the sanitary napkin 720 to displace the sanitary napkin 720 from the wearer's undergarment.

In the embodiments described above, the resilient element 215 is disposed within an air impermeable envelope. In still another embodiment, the resilient element 215 can be held in a compressed configuration by an envelope which is either air permeable or air impermeable. For example, one or both of the walls 232 and 234 can be air permeable, with the adhesive spacing W2 (FIG. 11) sized so that the walls 232 and 234 restrict expansion of the resilient element 215. The resilient element 215 can be expanded at the point of use of the disposable absorbent article by removing a portion of the envelope holding the resilient element 215 in a compressed configuration. For example, the resilient element 215 can be expanded by removing the wall 232 from the wall 234, such as by tearing or peeling. Referring to FIG. 8, in yet another embodiment, the envelope holding the resilient element 215 in a compressed configuration can comprise the wrapper 860. The resilient element 215 can be compressed as the sanitary napkin 720 and the wrapper 860 are folded as a unit about fold lines 852 and 853. The wrapper 860 is then sealed along edges 870 to maintain compression of the resilient element 215 within the folded and sealed wrapper 860. The resilient element 215 can then expand when the wrapper 860 is opened and removed from the sanitary napkin 720.

Figure 12:
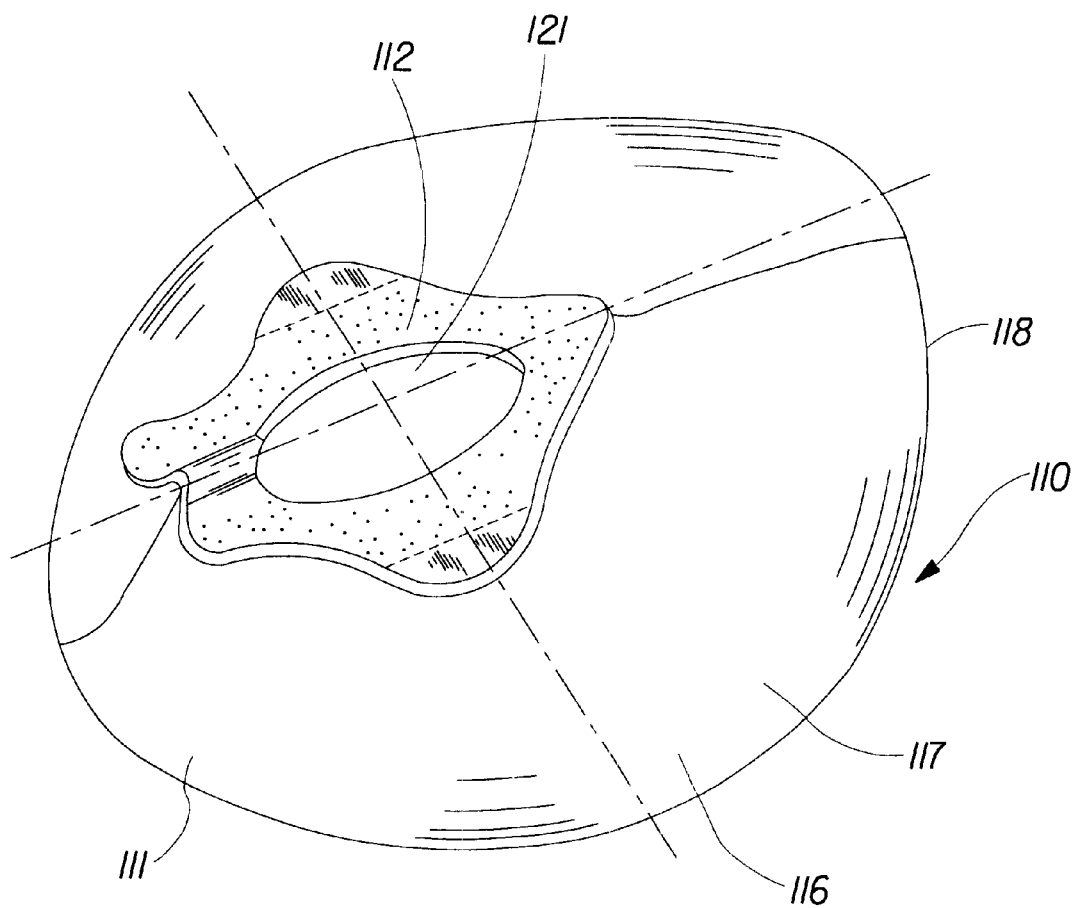
FIG. 12 is a perspective view of a fecal management device.
Figure 13:
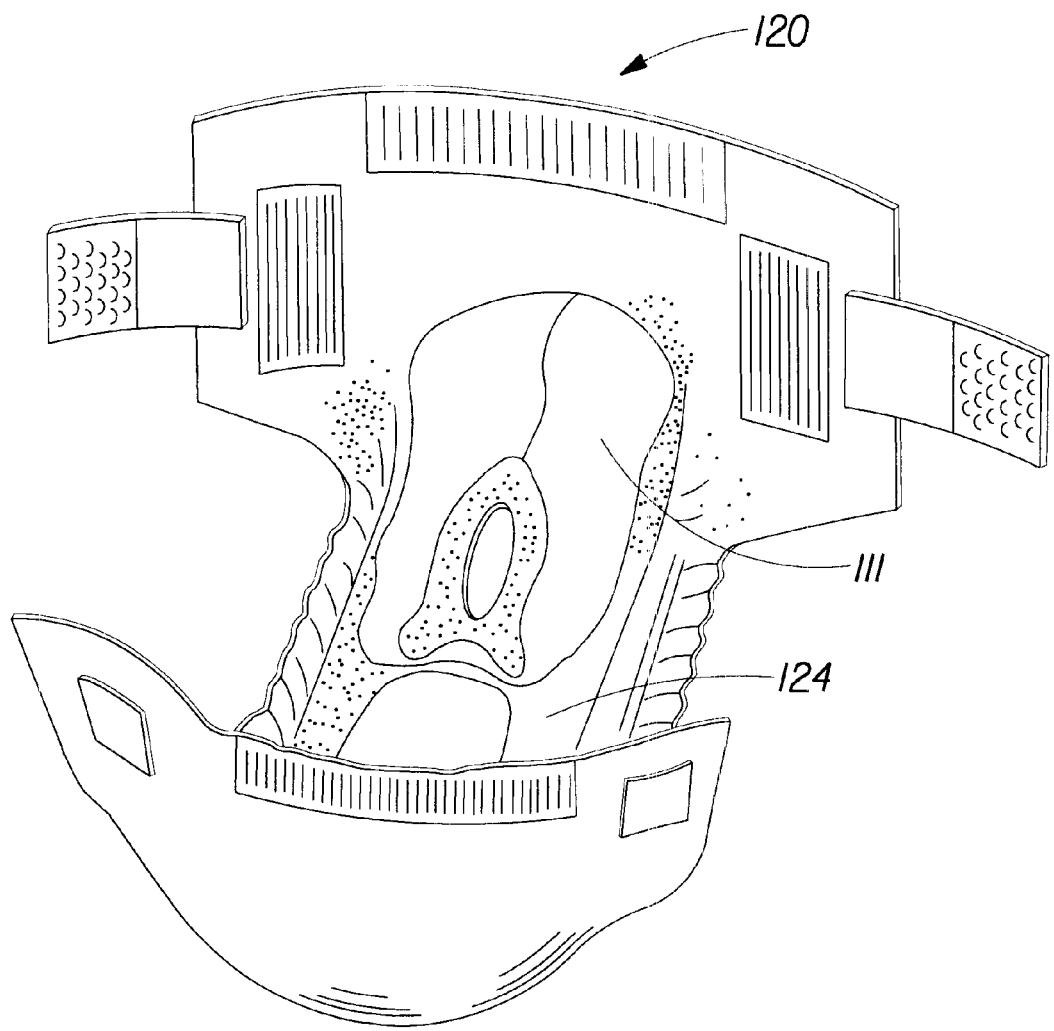
FIG. 13 is a perspective view or an absorbent article including a fecal management device.

Embodiments of the present invention may also include a waste management device 110 such as is shown in FIG. 12. The waste management device 110 may include a waste bag 111 to collect feces, urine or both. The waste bag 111 may have an aperture 121 and a flange 112 surrounding the aperture for preferably adhesive attachment to the perianal area of a wearer. Further, the waste management device 110 has been found to be particularly useful and beneficial when used in conjunction with a garment, or diaper, preferably a disposable diaper. One example of a diaper 120 including a waste bag 111 is shown in FIG. 13. If associated with a diaper 120 or other garment, the waste bag 111 may be disposed on or joined to any surface of the article. In one embodiment, the waste bag 111 is joined to the topsheet 124 of the diaper 120.

The waste bag 111 is preferably a flexible receptacle for the containment of excreted fecal matter or urine. Thus, the waste bag 111 is preferably liquid impermeable, and yet it may be breathable. Further, the waste bag 111 is designed of sufficient strength to withstand typical wearing conditions, such as sitting.

The waste bag 111 may comprise one or multiple layers. In one embodiment, the waste bag 111 may comprise three layers, preferably one film and two non-woven layers. The layers of the bag material may comprise any material, preferably so that the bag is liquid impervious. In a preferred embodiment of the present invention a laminate may be formed from a non-woven layer and a film.

Suitable film materials for any of the film layers preferably comprise a thermoplastic material. The thermoplastic material can may be vapor pervious or impervious and can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those described above with respect to the backsheet and monolithic breathable materials such as HYTREL™ available from DuPont and Pebax™ available from ELF Atochem, France.

The waste bag 111 may have any shape or size. Preferred shapes include flat circular type bags, cone shaped bags, truncated cone shaped bags and pyramidal or truncated pyramidal shaped bags and flat T shaped bags. Further, the waste bag 111 may be provided from a unitary piece of material or a number of separate pieces of material which may be identical or different and which may be sealed at their respective peripheries.

The waste bag 111 may also contain absorbent material. The absorbent material may comprise any absorbent material which is capable of absorbing and retaining liquids. The absorbent material may comprise a wide variety of liquid-absorbent materials commonly used in disposable diapers and other absorbent articles. Some examples are described herein with respect to the absorbent core.

The waste bag 111 is provided with an aperture 121 whereby fecal matter or urine is received from the body prior to storage within the bag cavity. The aperture 121 is preferably surrounded by a flange 112 and may be provided in any shape or size, such as circular, oblong, heart shaped and may be symmetrical or asymmetrical, preferably the aperture has an oblong configuration either in the longitudinal or in the transversal direction. The flange may comprise projections designed to fit the perineal, genital and/or coccygeal area of the wearer.

The flange 112 should be made of soft, flexible and malleable material to allow easy placement of the flange 112 to the perianal or uro-genital area. Typical materials include nonwoven materials, wovens, open celled thermoplastic foams, closed-cell thermoplastic foams, composites of open celled foams and stretch nonwoven, and films.

The waste bag 111 preferably further comprises an attachment means to secure the device to the wearer. Such means may comprise straps and or a body-compatible pressure sensitive adhesive applied to the wearer facing portion of the waste bag 111 or the flange. Any skin-friendly water resistant pressure sensitive adhesive may be used to attach the device to the perianal or uro-genital area of the wearer, such as hydrocolloid adhesives and hydrogel adhesives. Particularly effective adhesives in providing the desired adhesive properties to secure the flange to the skin of the wearer at the sensitive perianal area, while allowing for relatively painless application and removal, are formed from crosslinking polymers with a plasticiser to form a 3-dimensional matrix.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable absorbent article comprising:
   a backsheet;
   a topsheet joined to the backsheet;
   an absorbent core disposed intermediate the topsheet and the backsheet; and
   an expandable component disposed on the absorbent article, the expandable component comprising a compressed resilient element disposed within an air impermeable envelope having a port, the port comprising a gas-permeable component, the expandable component expandable from a first thickness to a second thickness greater than the first thickness upon opening of the air impermeable envelope.

2. The disposable absorbent article of claim 1 wherein the gas permeable component comprises a gas-permeable film.

3. The disposable absorbent article of claim 1 wherein the gas permeable film comprises a microporous film.

4. The disposable absorbent article of claim 1 wherein the gas permeable film comprises a monolithic film.

5. The disposable absorbent article of claim 1 wherein the expandable component expands to about 90% of original height reached in less than about 20 minutes.

6. The disposable absorbent article of claim 1 wherein the expandable component expands to about 90% of original height reached in not less than about 5 minutes.

7. The disposable absorbent article of claim 1 wherein the resilient element is porous.

8. The disposable absorbent article of claim 1 wherein the resilient element comprises an open celled foam.

9. The disposable absorbent article of claim 1 wherein the second thickness is at least about twice the first thickness.

10. The disposable absorbent article of claim 1 wherein the second thickness is at least about five times the first thickness.

11. The disposable absorbent article of claim 1 wherein the resilient element is disposed intermediate the topsheet and the backsheet.

12. The disposable absorbent article of claim 1 wherein the expandable component is joined to the backsheet.

13. The disposable absorbent article of claim 1 wherein the backsheet comprises at least a portion of the air impermeable envelope.

14. The disposable absorbent article of claim 1 wherein the disposable absorbent article comprises a disposable diaper, and wherein the expandable component comprises a spacer disposed intermediate the topsheet and the backsheet for maintaining a Z-direction fecal void space.

15. The disposable absorbent article of claim 14 wherein the topsheet has an aperture therethrough for receiving fecal matter, and wherein the spacer is registered with the aperture.

16. The disposable absorbent article of claim 14 wherein the spacer has an expanded shape comprising a generally U-shaped figure opening rearward.

17. The disposable absorbent article of claim 14 wherein the spacer has an expanded shape comprising a closed figure.

18. The disposable absorbent article of claim 1 wherein the expandable component comprises at least a portion of a seal for reducing the leakage of body exudates from between the disposable absorbent article and the wearer's skin.

19. The disposable absorbent article of claim 18 wherein the disposable absorbent article comprises a disposable diaper having front and rear waist regions, and wherein the expandable component is disposed in at least one of the front and rear waist regions.

20. The disposable absorbent article of claim 18 wherein the disposable absorbent article comprises a disposable diaper having side margins, and wherein the expandable component is disposed in at least one of the side margins.

21. The disposable absorbent article of claim 18 further comprising a leg cuff, and wherein the leg cuff comprises an expandable component.

22. The disposable absorbent article of claim 1 wherein the port includes a releasable closure.

23. The disposable absorbent article of claim 1 further including a waste bag joined to at least a portion of the article.

24. A disposable article for receiving bodily waste from a wearer, the disposable article including:
- a bag having an opening;
- an adhesive disposed about at least a portion of the opening of the bag; and
- an expandable component disposed in the article, the expandable component comprising a compressed resilient element disposed within an air impermeable envelope, the expandable component expandable from a first thickness to a second thickness greater than the first thickness upon opening of the air impermeable envelope.

25. The disposable article of claim 24 further including a flange joined to the bag and at least partially surrounding the opening of the bag, wherein the adhesive is disposed on at least a portion of the flange.

* * * * *

UNITED STATES PATENT AND TRADEMARK OFFICE
CERTIFICATE OF CORRECTION

PATENT NO. : 6,458,110 B1
DATED : October 1, 2002
INVENTOR(S) : Lavon et al.

It is certified that error appears in the above-identified patent and that said Letters Patent is hereby corrected as shown below:

Column 1,
Line 41, delete "is".

Column 3,
Line 40, delete "Ifs".

Column 8,
Line 60, delete "is".

Column 13,
Line 42, delete "is".

Column 14,
Line 4, delete "Hi" and insert -- H1 --.

Column 16,
Line 4, delete "carrier" and insert -- barrier --.

Signed and Sealed this

Twenty-seventh Day of April, 2004

JON W. DUDAS
*Acting Director of the United States Patent and Trademark Office*